(12) United States Patent
Hussain et al.

(10) Patent No.: US 6,380,175 B1
(45) Date of Patent: Apr. 30, 2002

(54) METHOD FOR ENHANCEMENT OF DELIVERY OF THC BY THE ADMINISTRATION OF ITS PRODRUGS VIA THE NASAL ROUTE

(75) Inventors: Anwar A. Hussain; Lewis W. Dittert, both of Lexington, KY (US); Ali M. Qaisi, Amman (JO); Ashraf Traboulsi, Lexington, KY (US)

(73) Assignee: New Millennium Pharmaceutical Research, Inc., Lexington, KY (US)

( * ) Notice: Subject to any disclaimer, the term of this patent is extended or adjusted under 35 U.S.C. 154(b) by 0 days.

(21) Appl. No.: 09/890,556
(22) PCT Filed: Feb. 4, 2000
(86) PCT No.: PCT/US00/03019
§ 371 Date: Aug. 2, 2001
§ 102(e) Date: Aug. 2, 2001
(87) PCT Pub. No.: WO00/45813
PCT Pub. Date: Aug. 10, 2000

Related U.S. Application Data

(60) Provisional application No. 60/118,695, filed on Feb. 4, 1999.

(51) Int. Cl.$^7$ .................. A61K 31/665; A61K 31/35; C07F 9/06
(52) U.S. Cl. .................. 514/100; 514/454; 549/220
(58) Field of Search .................. 549/220; 514/100, 514/454

(56) References Cited

U.S. PATENT DOCUMENTS

| | | |
|---|---|---|
| 4,933,363 A | 6/1990 | Elsohly |
| 5,508,037 A | 4/1996 | Elsohly |
| 6,008,383 A | 12/1999 | Elsohly |

*Primary Examiner*—Raymond Henley, III
(74) *Attorney, Agent, or Firm*—Burns, Doane, Swecker & Mathis LLP

(57) ABSTRACT

The present invention is directed to a method for enhancing the delivery of delta-9-tetrahydrocannabinol ("THC") to the brain of a mammal in need of treatment with this drug, by administering water-soluble prodrugs of THC intranasally.

42 Claims, No Drawings

METHOD FOR ENHANCEMENT OF DELIVERY OF THC BY THE ADMINISTRATION OF ITS PRODRUGS VIA THE NASAL ROUTE

This a 371 of PCT/US00/03019 filed Feb. 4,2000 which claims the benefit of U.S. Provisional Application No. 60/118,695 filed Feb. 4, 1999.

FIELD OF THE INVENTION

This invention relates generally to a method for enhancing the delivery of Δ-9-tetrahydrocannabinol ("THC") to the brain of a mammal in need of treatment with this drug, by administering water-soluble prodrugs of THC intranasally. More specifically, this invention relates to the enhancement of THC treatment by intranasal administration of water-soluble esters of THC. The invention is particularly useful as an anti-emetic, particulary to treat the nausea associated with anti-cancer chemotherapy.

BACKGROUND

The anti-emetic properties of THC are well-known. The lay press have advocated that marijuana (smoked) be made available for use as an anti-emetic, especially in cancer and AIDS patients who find it to be the only substance that controls their nausea while receiving chemotherapy. Unfortunately, marijuana smoke contains many of the carcinogenic substances that make tobacco smoke dangerous, and the toxicities associated with smoked marijuana are probably as great as those associated with tobacco smoking.

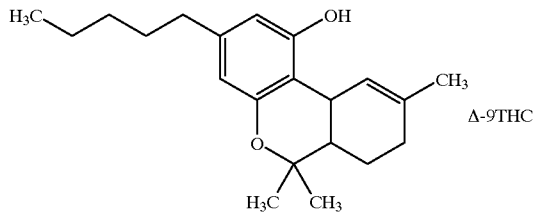

Oral THC is commercially available as the prescription product Marinol® Capsules. However, the oral absorption of THC from Marinol® Capsules is very slow and inefficient. It is estimated that less than half the oral dose of THC is absorbed, and the anti-emetic effects are not seen clinically until the second day after administration has begun. Thus, Marinol® Capsules are not useful unless taken chronically.

On the other hand, THC is rapidly and efficiently absorbed from marijuana smoke. It is likely that this rapid absorption is responsible for its clinical usefulness, i.e., a patient can offset nausea by smoking marijuana after the nausea begins to occur. The absorption of a variety of drugs with a variety of chemical structures from the nasal cavity of humans is known to produce blood concentrations similar to those observed following intravenous administration.

At room temperature, THC exists as a gummy, semisolid mass, which has very poor aqueous solubility. The physical properties of THC cause difficulties in the formulation of dosage forms suitable for human consumption. Certain dosage forms, e.g., injectables, cannot be prepared because of the physical nature of THC. The oral administration of THC is inefficient and highly variable resulting in an on-off therapeutic response and frequent serious side effects. There is a tremendous need for an improved dosage form for THC. Since THC is too insoluble in water, it cannot be administered nasally, transdermally, buccally, or sublingually.

In view of the foregoing, it is apparent that there exists a need in the art for improved methods of delivery of THC for treatment of nausea and prevention of emesis, in particular in connection with anti-cancer chemotherapy.

SUMMARY OF THE INVENTION

Accordingly, since THC is too insoluble in water to be used in conventional intranasal formulations, it is an object of the present invention to provide a method for alleviating nausea comprising intranasal administration of water soluble prodrugs of THC. The prodrug esters of THC described herein are sufficiently water-soluble to allow the formulation of any desired dosage form and are more readily absorbed into the systemic circulation, i.e., are more bio-available than THC itself.

An intranasal dosage form containing a water-soluble prodrug ester of THC that would rapidly deliver an effective does of THC to the blood following administration would have the same anti-emetic benefits as marijuana smoke but without the toxicities associated with smoke products.

It is a further aspect of this invention to provide a method for administering THC in a manner which significantly enhances plasma levels of THC, and thus its bioavailability, compared to prior art methods.

It is a further aspect of this invention to provide a method for administering THC which provides for enhanced delivery of THC directly to the central nervous system, its intended site of action.

In addition to intranasal dosage forms, the prodrug esters described in the present application also lend themselves to formulation into dosage forms designed to be administered orally, by injection, transdermally, or by any other conceivable routes. In particular, water-soluble derivatives that exist as crystalline solids would lend themselves readily to formulation into oral tablets, capsules, and liquids.

It is a still further aspect of this invention to provide a method for administering THC which minimizes the side-effects associated with conventional THC administration. This object has been achieved in the present invention by the nasal administration of water-soluble esters of THC.

It is a still further aspect of this invention to provide a method for administering THC which is equal or superior to intravenous administration in many respects, including effectiveness, but which avoids many of the problems associated with the intravenous route, including the "on-off effect," combined with superior ease of administration.

A further aspect of this invention is to provide a pharmaceutical composition suitable for intranasal administration, for treatment of nausea and emesis, particularly associated with anti-cancer chemotherapy. Accordingly, a composition according to the present invention comprises a water-soluble prodrug of THC and a pharmaceutically acceptable carrier therefor.

With the foregoing and other objects, advantages and features of the invention that will become hereinafter apparent, the nature of the invention may be more clearly understood by reference to the following detailed description of the preferred embodiments of the invention and to the appended claims.

DETAILED DESCRIPTION OF THE PREFERRED EMBODIMENTS OF THE INVENTION

The present inventors have discovered a novel method for the treatment of nausea and prevention of emesis, by the intranasal administration of a water-soluble prodrug of THC. This method offers significant clinical advantages over the prior art. More specifically, the inventors sought to provide a safe, effective and convenient treatment for nausea and vomiting associated with anti-cancer chemotherapy which comprises the administration of water-soluble prodrugs of THC intranasally, thus avoiding the side-effects associated with oral dosage forms.

A prodrug is a compound formed by chemical modification of a biologically active compound which will liberate the active compound in vivo by enzymatic or hydrolytic cleavage. Advantages of this approach include reduction of general cytotoxicity, better bioavailability of active drug or longer duration of action. Any water soluble prodrug of THC is useful in the practice of this present invention.

The inventors have found that intranasal administration of esters of THC, i.e., prodrugs of THC, are particularly preferred in the practice of the present invention. Intranasal administration of these compounds is as effective as oral or intravenous administration of THC, but may be conveniently and painlessly self-administered by the patient.

Preferred THC esters include alkyl, cycloalkyl, and aryl esters, particularly methyl, butyl, pentyl, cyclohexyl, and benzyl esters, and pharmaceutically acceptable salts thereof.

Pharmaceutically acceptable salts of an acid group or an amino group include, but are not limited to, salts of organic carboxylic acids such as acetic, lactic, tartaric, malic, isothionic, lactobionic and succinic acids; organic sulfonic acids such as methanesulfonic, ethanesulfonic, benzenesulfonic and p-tolylsulfonic acids, and inorganic acids such as hydrochloric, sulfuric, phosphoric and sulfamic acids.

In a preferred embodiment, a compound according to the present invention is a THC amine-ester prodrug having, for example, a structure according to Formula (I)

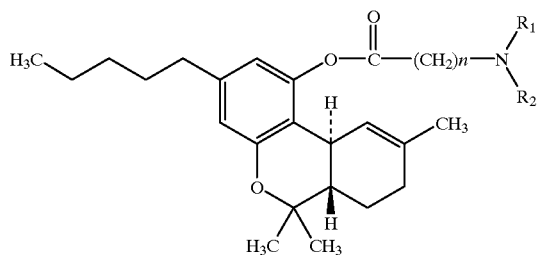

(I)

wherein n=1 to 10; and $R_1$ and $R_2$ are both alkyl, or together are members of a saturated ring.

In an alternative embodiment, a compound according to the present invention is a hemiester THC prodrug having, for example, a structure according to Formula (II):

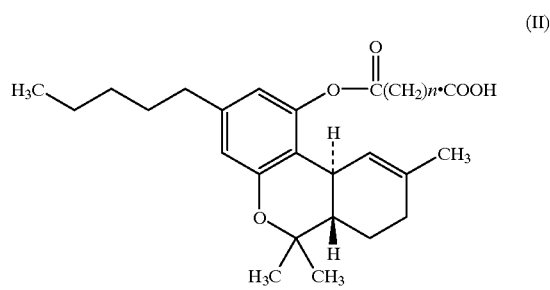

(II)

wherein n 1 to 10.

In another alternative embodiment, a compound according to the present invention is a phosphate ester THC prodrug having, for example, a structure according to Formula (III):

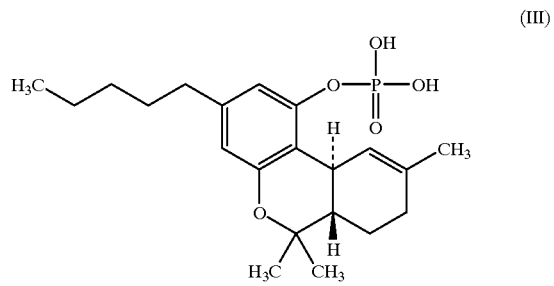

(III)

A still further aspect of this invention is a pharmaceutical composition of matter for treating nausea and vomiting that comprises at least one THC ester as described above, mixtures of THC esters thereof, and/or pharmaceutical salts thereof, and pharmaceutically acceptable carriers therefor. Such compositions are prepared in accordance with accepted pharmaceutical procedures, for example, as described in *Remington's Pharmaceutical Sciences*, seventeenth edition, ed. Alfonso R. Gennaro, Mack Publishing Company, Easton, Pa., Eighteenth edition (1990).

For therapeutic use in a method of treating nausea, a THC ester, or its salt, can be conveniently administered in the form of a pharmaceutical composition containing a THC ester, or its salt, and a pharmaceutically acceptable carrier therefor. Suitable carriers are well known to those skilled in the art and vary with the desired form and mode of administration of the pharmaceutical composition. Typically, the carrier may be a liquid, suspension, semi-solid, or vaporizable carrier, or combinations thereof. In a preferred embodiment, the carrier is a pharmaceutically acceptable aqueous carrier.

The compound of the invention or its salt may be formulated together with the carrier into any desired unit dosage form. Unit dosage forms such as solutions, suspensions, and water-miscible semisolids are particularly preferred.

Each carrier must be "acceptable" in the sense of being compatible with the other ingredients in the formulation and not injurious to the patient. The carrier must be biologically acceptable and inert, i.e., it must permit the body's metabolic reactions to effectively transform the esters of this invention into THC. To prepare formulations suitable for intranasal administration, solutions and suspensions are sterilized and are preferably isotonic to blood.

The formulations may conveniently be presented in unit dosage form and may be prepared by any method known in the art. Such methods include the step of bringing the active ingredient into association with the carrier which itself may encompass one or more accessory ingredients. In general, the formulations are prepared by uniformly and intimately bringing into association the active ingredient with liquid carriers or finely divided solid carriers or both, and then if necessary shaping the product. Various unit dose and multidose containers, e.g., sealed ampules and vials, may be used, as is well known in the art.

In addition to the ingredients particularly mentioned above, the formulations of this invention may also include other agents conventional in the art for this type of pharmaceutical formulation.

Also part of this invention is a method of treating nausea and preventing emesis, particularly that associated with anti-cancer chemotherapy, in a mammal, e.g., human, by treating that mammal with an effective amount of a THC ester intranasally. In this application patient will encompass any mammal suffering from nausea or vomiting, particularly a mammal undergoing anti-cancer chemotherapy.

The dosage of the THC esters, pharmaceutically acceptable salts thereof, or mixtures thereof, in the compositions of the invention administered to a patient will vary depending on several factors, including, but not limited to, the age, weight, and species of the patient, the general health of the patient, the severity of the symptoms, whether the composition is being administered alone or in combination with other agents, the incidence of side effects and the like. The desired dose may be administered as 1 to 6 or more subdoses administered at appropriate intervals throughout the day. The compounds may be administered repeatedly over a period of months or years, or it may be slowly and constantly infused to the patient. Higher and lower doses may also be administered.

The daily dose may be adjusted taking into account, for example, the above-identified variety of parameters. Typically, the present compositions may be administered in an amount of about 1 to 50 mg/kg body weight. However, other amounts may also be administered.

To achieve good plasma concentrations, the active compounds may be administered, for instance, by intranasal administration of an approximate 0.1 to 1M solution of the active ingredient, optionally in saline.

While it is possible for the active ingredient to be administered alone, it is preferably present as a pharmaceutical formulation. The formulations of the present invention comprise at least one active ingredient, as defined above, together with one or more acceptable carriers thereof and optionally other therapeutic agents.

The above method may be practiced by administration of the compounds by themselves or in a combination with other active ingredients in a pharmaceutical composition. Other therapeutic agents suitable for use herein are any compatible drugs that are effective by the same or other mechanisms for the intended purpose, or drugs that are complementary to those of the present agents. Agents effective against chemotherapy-induced emesis include D2/5HT$_3$ antagonists such as substituted benzamides (e.g., metoclopramide, trimethobenzamide); 5HT$_3$ antagonists (e.g., ondansetron, granisetron, tropisetron, dolasetron); D2 antagonists, such as the phenothiazines (e.g., chlorpromazine, perphenazine, proclorperazine, promethazine, thiethylperazine, triflupromazine), benzimidazole derivatives (e.g., domperidone), and butyrophenones (e.g., haloperidol, droperidol); corticosteroids (e.g., dexamethasone, methylprednisolone); and other cannabinoids (e.g., nabilone). The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained. The therapeutic method of the invention may be used in conjunction with other therapies as determined by the practitioner.

Having now generally described this invention, the same will be better understood by reference to certain specific examples, which are included herein for purposes of illustration only and are not intended to be limiting of the invention or any embodiment thereof, unless so specified.

EXAMPLE 1

General Method of Synthesis of THC Esters

Typically, the prodrug esters of THC may be prepared using a modification of the procedure below. One hundred ml of the appropriate alcohol are placed in a 200-ml three-necked flask equipped with a reflux condenser. The alcohol is cooled to $-10°$ C. and nitrogen is bubbled through for 10 min. Thionyl chloride (15 ml) is then added slowly over 15 min, and the reaction mixture is stirred for an additional 15 min. After stirring, 4 g of THC is added, and the mixture is refluxed at $60°$ C. for 12 hr. The ester hydrochloride is precipitated by adding enough petroleum ether to make the solution turbid and then placing the mixture in a refrigerator ($4°$ C.) overnight. The final product is collected by filtration and is recrystallized from an acetone-petroleum ether mixture. The crystals are dried in a vacuum desiccator at room temperature and stored in a desiccator until used. The structure and purity of each ester hydrochloride of THC may be confirmed by NMR spectra, HPLC, melting point, and elemental analysis.

EXAMPLE 2

Stability and Physicochemical Properties of the Ester Prodrugs in Aqueous Buffers Analytical Procedures High-performance liquid chromatography (HPLC) is used for determining physicochemical properties (i.e., chemical stability, partition coefficient etc.). All samples are run at ambient temperature. The resulting chromatograms are recorded on an integrator. Each chromatogram is accompanied by a printout of the peak area, retention time, and the percentage of the total area of each peak.

Analytical Methodology

To determine physicochemical properties (i.e., chemical stability, partition coefficient, etc.), the following HPLC system is used: Beckman 110B Solvent Delivery Module, Spectroflow 757 Absorbance Detector, Spectra-Physics DataJet Integrator, Waters 712 WISP Autoinjector, Waters Nova-Pak $C_8$ column (3.9 mm×150 mm).

The mobile phase consists of 0.05M phosphate buffer at pH 4.0 and acetonitrile. The acetonitrile portion is adjusted according to the ester (see below). The flow rate is set at 1.0 ml/min. The UV wavelength is set at 280 nm.

The reactions are initiated by preparing 0.2 mg/ml solutions of the butyl ester prodrug in 0.05M, 0.20M, and 0.50M phosphate buffers at pH 3.5, 5.5, and 7.4. The solution is kept in screw-capped culture tubes at $20°$ C. and $37°$ C. At appropriate time intervals, samples are taken and kept on ice until analysis.

The rate of hydrolysis of each ester is determined from the slope of the linear plot of the logarithm of the residual ester concentration against time. Preferably, the experiments are run at least in triplicate for each ester. The pH is determined after each experiment.

The rate constants are calculated and the activation energy obtained. The pH of optimum stability and the shelf-life at that pH is calculated.

Partition Coefficients

The apparent partition coefficient of each ester is determined at room temperature (20° C.) between 1-octanol and pH 7.4, 0.05M phosphate buffer. The phosphate buffer and octanol are presaturated with one another before use to minimize the volume change due to mutual solubility. An aqueous phase (5 ml) containing 0.4 mg/ml ester prodrug solution is mixed with 5 ml of 1-octanol. The mixture is manually shaken for 2 minutes followed by mechanical shaking at 20° C. for 1 hour to ensure equilibrium. After centrifugation, the ester concentration in the aqueous phase is measured by HPLC. The partition coefficient is calculated by subtracting the final aqueous phase concentration from the initial aqueous phase concentration to calculate the final octanol phase concentration. The partition coefficient is then calculated by dividing the final aqueous phase concentration into the final octanol phase concentration.

Solubility

An excess amount of THC and the esters of THC are equilibrated with pH 7.4, 0.05M phosphate buffer in screw-cap vials with constant shaking, vortexing, and sonicating for about one hour. The saturated solutions are filtered through 0.2 $\mu$m filter, and the filtrates are analyzed by HPLC.

EXAMPLE 3

In-vitro Enzymatic Hydrolysis Studies

Analytical Procedures

The HPLC system for in vitro enzymatic studies also includes: Applied Biosystems Solvent Delivery System 400, Fluorescence Detector 980; ABI Analytical Kratos Division Spectroflow Static Mixer/injector model 491; SpectraPhysics DataJet Integrator; Shimadzu Auto-Injector SIL-6A, Whatman Partisil 5 SCX column (4.6 mm×100 mm), Whatman CO:PEL ODS Guard column (2 mm×70 mm).

The mobile phase consists of 0.05M phosphate buffer at pH 2.6, and acetonitrile, containing ethylenediaminetetraacetic acid disodium salt dehydrate 20 mg/l. The acetonitrile portion may be adjusted according to the ester. The flow rate is set at 1.0 ml/min. The excitation wavelength is set at 282 nm and the emission wavelength is set at 310 nm.

Rat Plasma

Five 200 $\mu$l aliquot parts of rat plasma are added to five 100 $\mu$l of a 0.05M, pH 6.0 phosphate buffer solution containing 1 mg/ml of each ester and the samples incubated at 37° C. The reactions are quenched at various times by adding 200 $\mu$l of acetonitrile. The samples are centrifuged for 2 minutes. The supernatant is filtered through a 0.45 $\mu$m filter and injected directly onto the HPLC.

The rate of hydrolysis of each ester is determined from the slope of the linear plot of the logarithm of the residual ester concentration against time.

Rat Brain Homogenate

One part of whole rat brain tissue is homogenized with 5 parts of saline using a tissue grinder. Five 200 $\mu$l aliquot parts of brain homogenate are added to five 100 $\mu$l of a 0.05M, pH 6.0 phosphate buffer solution containing 1 mg/ml of the appropriate ester and incubated at 37° C. The reactions are quenched at various times by adding 200 $\mu$l of acetonitrile. The samples are centrifuged for 2 minutes. The supernatant is filtered through a 0.45 $\mu$m filter and injected directly onto the HPLC.

The rate of hydrolysis of each ester is determined from the slope of the linear plot of the logarithm of the residual ester concentration against time.

Rat Cerebrospinal Fluid

Five 50 $\mu$l aliquot parts of rat CSF are added to five 50 $\mu$l of a 0.05M, pH 6.0 phosphate buffer solution containing 1 mg/ml of the butyl ester and the samples incubated at 37° C. The reactions are quenched at various times by adding 200 $\mu$l of acetonitrile. The samples are centrifuged for 2 minutes. The supernatant is filtered through a 0.45 $\mu$m filter and injected directly into the HPLC.

The rate of hydrolysis of butyl ester is determined from the slope of the linear plot of the logarithm of the residual ester concentration against time.

Rat Nasal Perfusate

Nasal perfusate is obtained from the rat nasal cavity by circulating 3 ml of saline into one nostril and collecting the saline solution from the other nostril. Circulating time is 3 minutes. The hydrolysis study is performed immediately following perfusion. Five 200 $\mu$l aliquot parts of rat nasal perfusate are added to five 100 $\mu$l of a 0.05M, pH 6.0 phosphate buffer solution containing 1 mg/ml of the butyl ester and the samples incubated at 37° C. The reactions are quenched at various times by adding 200 $\mu$l of acetonitrile. The samples are centrifuged for 2 minutes. The supernatant is filtered through a 0.45 $\mu$m filter and injected directly into the HPLC.

The rate of hydrolysis of butyl ester is determined from the slope of the linear plot of the logarithm of the residual ester concentration against time.

EXAMPLE 4

In vivo Studies

The nasal absorption of THC & THC prodrugs may be studied using the in vivo experimental technique described below.

Analytical Procedures for the in vivo Studies

The HPLC system for in vivo studies includes: Applied Biosystems Solvent Delivery System 400, Applied Biosystems 429A Integrator, ABI Analytical Kratos Division Spectroflow Static mixer/injector model 591; BAS Amperometric Detector LC-4B (operated at +0.8 V vs. a Ag/AgCl reference electrode), TOSOH TSK-GEL ODS-80Tm column (4.6 mm×150 mm), Whatman CO:PEL ODS Guard column (2 mm×70 mm).

THC and THC esters are measured in plasma, brain, and cerebrospinal fluid (CSF) by a previously reported high performance liquid chromatographic (HPLC) procedure using an electrochemical detector, with a slight modification. The mobile phase consists of 0.05M phosphate buffer at pH 2.9, heptane sulfonate sodium salt 500 mg/l, and ethylenediaminetetraacetic acid disodium salt dehydrate 15 mg/l. The flow rate is set at 1.5 ml/min.

Male Sprague-Dawley rats weighing 250–275 gm are used. Animals are fasted overnight before the experiment, but water is given ad libitum. All surgical procedures are performed under anesthesia i.e., intraperitoneal injection of pentobarbital (40 mg/kg). An incision is made in the neck, and the trachea is cannulated with a polyethylene tube. A closed tube is inserted through the esophagus to the posterior part of the nasal cavity.

The nasopalatine passage is closed with an adhesive agent to prevent drainage of the drug from the nasal cavity to the mouth.

Blood samples are collected from a cannula inserted into the femoral artery. For intravenous administration, the jugular vein is cannulated for administering the dose.

To determine the residual amount of drug in the nasal cavity, the cavity is washed with 2 ml of 0.05M, pH 6.0 phosphate buffer. The drug concentration is then determined by HPLC.

Preparation of the Solutions

Ester prodrug solutions at 4, 20, and 40 mg/kg/0.2 ml equimolar doses of THC are freshly prepared by using 0.05M phosphate buffer at pH 6.0.

Solutions of THC are prepared by first dissolving the compound in 1 N hydrochloric acid then using 0.5M phosphate buffer at pH 7.4 to adjust the 15 solution to pH 4.

For nasal administration, aqueous solutions of THC or equimolar prodrugs are administered through the nostril using a microsyringe. For intravenous administration, the same dose of the drug is injected through the jugular vein.

Sample Collection after Nasal and Intravenous Administrations

For intravenous administration studies, blood samples are collected at 0, 2, 5, 10, 15, 30, 45, 60, 90, and 120 minutes. For nasal administration studies, blood samples are collected at 0, 5, 10, 15, 20, 30, 40, 60, 90, and 120 minutes. After immediate centrifugation (3000×g for 3 min), the plasma is separated. The animal is sacrificed after the last sample is obtained and the brain is carefully removed. The olfactory bulb and striatum are carefully separated from the brain. Purification of the biological samples for THC analysis is carried out using a modified alumina adsorption procedure (described in Section 4.1) and the samples are then analyzed by HPLC.

Extraction of THC

Plasma samples are mixed with 5 µl of 2% $Na_2EDTA$ and 5 µl of 5% sodium metabisulfite in normal saline. The samples are kept frozen until extraction. THC is isolated by a modification of the alumina adsorption procedure of A. H. Anton. (Alumina activation is mentioned in Section 4.1) Each plasma sample (50 µl) is mixed with 70 mg of activated aluminum gel, 0.2 ml of 2M Tris buffer (pH 8.6), 0.1 ml of 2N NaOH, and 10 µl of 3,4-dihydroxybenzylamine aqueous solution as an internal standard in a glass test-tube for 30 min. After mixing, the alumina is washed once with 8 ml of 10 mM Tris buffer (pH 8.6) and twice with 8 ml of distilled water adjusted to pH 7.0 with 0.1N NaOH. After the water is aspirated, THC is eluted with 0.3 ml of 0.8N HCl. The samples obtained are frozen until HPLC analysis.

While the invention has been described herein by references to various specific materials, procedures, and examples, it is understood that the invention is not restricted to the particular materials, combinations of materials, and procedures selected for that purpose. Numerous variations of such details can be implied and will be appreciated by those skilled in the art.

What is claimed is:

1. An antiemetic amine ester of Δ9-THC, wherein said ester has the structure of Formula (I):

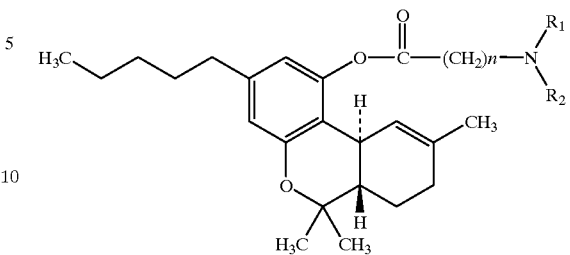

(I)

wherein
n=1 to 10; and
$R_1$ and $R_2$ are both alkyl, or together are members of a saturated ring.

2. A composition comprising an antiemetic compound according to claim 1 and a carrier therefor.

3. A composition according to claim 2, wherein said carrier is a pharmaceutically acceptable carrier.

4. A composition according to claim 2, further comprising a second antiemetic agent.

5. A composition according to claim 4, wherein the second antiemetic agent comprises $D2/5HT_3$ antagonists, $5HT_3$ antagonists, D2 antagonists, or corticosteroids, or mixtures thereof.

6. A composition according to claim 5, wherein the $D2/5HT_3$ antagonists comprise metoclopramide and/or trimethobenzamide.

7. A composition according to claim 5, wherein the $5HT_3$ antagonists comprise ondansetron, granisetron, tropisetron, or dolasetron, or mixtures thereof.

8. A composition according to claim 5, wherein the D2 antagonists comprise phenothiazines, benzimidazole derivatives, or butyrophenones, or mixtures thereof.

9. A composition according to claim 8, wherein the phenothiazines comprise chlorpromazine, perphenazine, proclorperazine, promethazine, thiethylperazine, or triflupromazine, or mixtures thereof.

10. A composition according to claim 8, wherein the benzimidazole derivative is domperidone.

11. A composition according to claim 8, wherein the butyrophenones comprise haloperidol and/or droperidol.

12. A composition according to claim 5, wherein the corticosteroids comprise dexamethasone and/or methylprednisolone.

13. An antiemetic hemiester of Δ9-THC, wherein said ester has the structure of Formula (II):

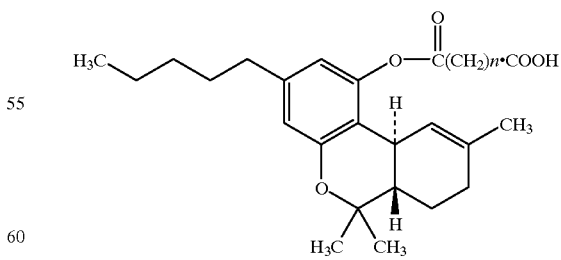

(II)

wherein n=1 to 10.

14. A composition comprising an antiemetic compound according to claim 13 and a carrier therefor.

15. A composition according to claim 14, wherein said carrier is a pharmaceutically acceptable carrier.

16. A composition according to claim 14, further comprising a second antiemetic agent.

17. A composition according to claim 16, wherein the second antiemetic agent comprises D2/5HT$_3$ antagonists, 5HT$_3$ antagonists, D2 antagonists, or corticosteroids or mixtures thereof.

18. A composition according to claim 17, wherein the D2/5HT$_3$ antagonists comprises metoclopramide and/or trimethobenzamide.

19. A composition according to claim 17, wherein the 5HT$_3$ antagonists are selected from the group comprising of ondansetron, granisetron, tropisetron, or dolasetron, or mixtures thereof.

20. A composition according to claim 17, wherein the D2 antagonists comprise phenothiazines, benzimidazole derivatives, or butyrophenones or mixtures thereof.

21. A composition according to claim 20, wherein the phenothiazines are selected from the group comprising chlorpromazine, perphenazine, proclorperazine, promethazine, thiethylperazine, or triflupromazine or mixtures thereof.

22. A composition according to claim 20, wherein the benzimidazole derivative is domperidone.

23. A composition according to claim 20, wherein the butyrophenones comprise haloperidol and/or droperidol.

24. A composition according to claim 17, wherein the corticosteroids comprise dexamethasone and/or methylprednisolone.

25. A phosphate ester of Δ9-THC, wherein said ester has the structure of Formula (III):

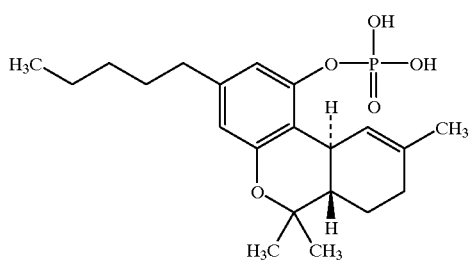

(III)

26. A composition comprising an antiemetic compound according to claim 25 and a carrier therefor.

27. A composition according to claim 26, wherein said carrier is a pharmaceutically acceptable carrier.

28. A composition according to claim 26, further comprising a second antiemetic agent.

29. A composition according to claim 28, wherein the second antiemetic agent comprises D2/5HT$_3$ antagonists, 5HT$_3$ antagonists, D2 antagonists, or corticosteroids, or mixtures thereof.

30. A composition according to claim 29, wherein the D2/5HT$_3$ antagonists comprise metoclopramide and/or trimethobenzamide.

31. A composition according to claim 29, wherein the 5HT$_3$ antagonists comprise ondansetron, granisetron, tropisetron, or dolasetron, or mixtures thereof.

32. A composition according to claim 29, wherein the D2 antagonists comprise phenothiazines, benzimidazole derivatives, or butyrophenones, or mixtures thereof.

33. A composition according to claim 32, wherein the phenothiazines comprise chlorpromazine, perphenazine, proclorperazine, promethazine, thiethylperazine, or triflupromazine, or mixtures thereof.

34. A composition according to claim 32, wherein the benzimidazole derivative is domperidone.

35. A composition according to claim 32, wherein the butyrophenones comprise haloperidol and/or droperidol.

36. A composition according to claim 29, wherein the corticosteroids comprise dexamethasone and/or methylprednisolone.

37. A method for preventing or treating the nausea and/or vomiting following administration of an anti-cancer chemotherapeutic agent comprising intranasally administering to a patient in need of such prevention or treatment an effective amount of an antiemetic compound according to claim 1 to inhibit nausea and/or vomiting.

38. The method of claim 37, wherein the antiemetic compound is administered in a dose of 1 to 50 mg/kg body weight.

39. A method for preventing or treating the nausea and vomiting following administration of an anti-cancer chemotherapeutic agent comprising intranasally administering to a patient in need of such prevention or treatment an effective amount of an antiemetic compound according to claim 13 to inhibit nausea and vomiting.

40. The method of claim 39, wherein the antiemetic compound is administered in a dose of 1 to 50 mg/kg body weight.

41. A method for preventing or treating the nausea and vomiting following administration of an anti-cancer chemotherapeutic agent comprising intranasally administering to a patient in need of such prevention or treatment an effective amount of an antiemetic compound according to claim 25 to inhibit nausea and vomiting.

42. The method of claim 41 wherein the antiemetic compound is administered in a dose of 1 to 50 mg/kg body weight.

* * * * *